Figure 1:
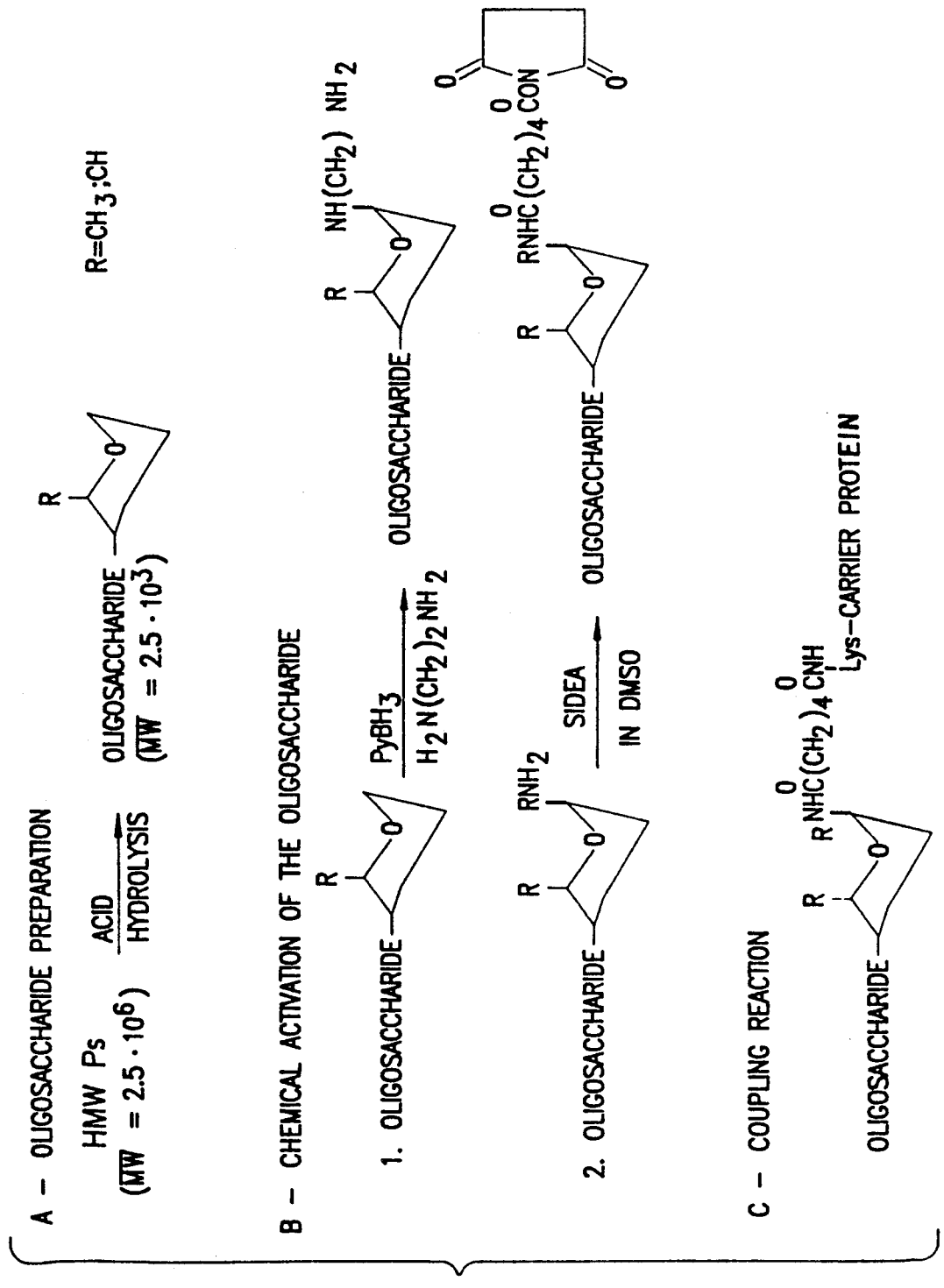

United States Patent [19]

Porro

[11] Patent Number: 5,306,492
[45] Date of Patent: Apr. 26, 1994

[54] OLIGOSACCHARIDE CONJUGATE VACCINES

[75] Inventor: Massimo Porro, Siena, Italy

[73] Assignee: American Cyanamid Company, Wayne, N.J.

[21] Appl. No.: 921,678

[22] Filed: Jul. 30, 1992

Related U.S. Application Data

[62] Division of Ser. No. 590,649, Sep. 28, 1990, Pat. No. 5,153,312.

[51] Int. Cl.$^5$ .................. A61K 39/385; A61K 39/02; C07K 17/06
[52] U.S. Cl. ...................... 424/88; 424/92; 530/404; 530/405
[58] Field of Search .............. 424/88, 92; 530/404, 530/405

[56] References Cited

U.S. PATENT DOCUMENTS

| | | | |
|---|---|---|---|
| 4,057,685 | 11/1977 | McIntire | 536/18 |
| 4,314,988 | 2/1982 | Farina et al. | 424/111 |
| 4,356,170 | 10/1982 | Jennings | 424/92 |
| 4,619,828 | 10/1986 | Gordon | 424/92 |
| 4,663,160 | 5/1986 | Tsay et al. | 424/87 |
| 4,711,779 | 12/1987 | Porro et al. | 424/92 |
| 4,761,283 | 8/1988 | Anderson | 424/92 |
| 4,808,700 | 2/1989 | Anderson | 530/403 |
| 4,830,852 | 5/1989 | Marburg | 424/858 |
| 5,034,519 | 12/1987 | Beuvery | 536/117 |
| 5,153,312 | 10/1992 | Porro | 530/405 |

OTHER PUBLICATIONS

Chu et al., (1982), J. Immunol. Methods 55:73–78.
Aldrich 1990–1991 Catalog p. 177 Product No. 17,975-2 of Borane-Pyridine Complex.
Schneerson et al., J. Experimental Medicine 152: 361–376 (1980).
Geyer et al., Med Microbiol. Immunol. 165: 271–288 (1979).
Anderson, Infection and Immunity 39: 233–238 (1983).
Snippe et al., Infection and Immunity 42: 842–844 (1983).
Porro et al., Medecine Tropicale, 43: 129–132 (1983).
Schwartz, B. A. et al., Arch Biochem. & Biophysics 181: 542–549 (1977).
Chu, C. et al. Invection and Immunity 40, No. 1, pp. 245–256 (1983).
Porro et al., Molecular Immunology 22(8): 907–919 (1985).

*Primary Examiner*—Kay K. Kim
*Attorney, Agent, or Firm*—Kenneth J. Dow

[57] ABSTRACT

The present invention relates to an improved method for producing oligosaccharide conjugate vaccines. In an additional aspect of the invention, oligosaccharide vaccines are produced which elicit a monospecific and homogeneous immune response to capsular polysaccharide. A specific embodiment of the invention provides for vaccines which induce immunity to prevalent serotypes of *Streptococcus pneumoniae*.

2 Claims, 4 Drawing Sheets

5,306,492

OLIGOSACCHARIDE CONJUGATE VACCINES

This is a divisional of co-pending application Ser. No. 07/590,649, filed on Sep. 28, 1990, now U.S. Pat. No. 5,153,312.

TABLE OF CONTENTS

1. Introduction
2. Background of the Invention
    2.1. Diseases Caused By *Streptococcus Pneumoniae*
    2.2. Pneumococcal Vaccines
    2.3. Conjugate Vaccines
        2.3.1. Intact Capsular Polymers As Antigens In Vaccines
        2.3.2. Use Of Carrier Proteins To Make Antiserum To Haptens
        2.3.3. Vaccines Containing Conjugates
        2.3.4. Method For Preparing Conjugate Vaccines
3. Summary Of The Invention
    3.1. Abbreviations and Definitions
4. Brief Description Of The Figures
5. Detailed Description Of The Invention
    5.1. Preparation Of Oligosaccharides
    5.2. Activation Of Oligosaccharides
    5.3. Conjugation Of Oligosaccharides To Protein
    5.4. Immunochemical Characterization Of Glycoconjugates
    5.5. Vaccine Formulation And Administration
    5.6. Utility Of Oligosaccharide Conjugate Vaccines
6. Example: Development Of A Multivalent Pneumococcal Oligosaccharide Conjugate
    6.1. Preparation Of Polysaccharide
    6.2. Hydrolysis Of Polysaccharide
        6.2.1. Hydrolysis of *S. Pneumoniae* Type 6A Polysaccharide
        6.2.2. Hydrolysis of *S. Pneumoniae* Type 14 Polysaccharide
        6.2.3. Hydrolysis of *S. Pneumoniae* Type 19F Polysaccharide
        6.2.4. Hydrolysis of *S. Pneumoniae* Type 23F Polysaccharide
    6.3. Immunochemical Characterization Of *S. Pneumoniae* Oligosaccharide Haptens
    6.4. Activation Of The End-Reducing Unit Of *S. Pneumoniae* Oligosaccharides
    6.5. Conjugation Of Activated Oligosaccharide to $CRM_{197}$ Protein
        6.5.1. Preparation Of $CRM_{197}$ Protein
        6.5.2. Conjugation Of Activated Oligosaccharides
            6.5.2.1. Comparison Of The Efficiency Of Conjugation Using As Linker The Succinimidyl Diester Of Adipic Acid Versus The Succinimidyl Diester of Succinic Acid
    6.6. Immunogenicity of *S. Pneumoniae* Glycoconjugates
    6.7. Oligosaccharides of Chain Length $\overline{DP}=10$-$20$ Are Suboptimally Immunogenic
    6.8. The Immune Response To The Glycoconjugates Is Monospecific And Homogeneous

1. INTRODUCTION

The present invention relates to an improved method for producing oligosaccharide conjugate vaccines. In an additional aspect of the invention, oligosaccharide vaccines are produced which elicit a monospecific and homogeneous immune response to capsular polysaccharide. A specific embodiment of the invention provides for vaccines which induce immunity to prevalent serotypes of *Streptococcus pneumoniae* which may be particularly important for use in pediatric patients as well as the elderly and those with reduced immunity due to infirmity or disease (including for example, AIDS patients).

2. BACKGROUND OF THE INVENTION

2.1. Diseases Caused by Streptococcus pneumoniae

The pneumoccus (*Streptococcus pneumoniae*) is a gram-positive encapsulated coccus that usually grows in pairs or short chains. In the diplococcal form, the adjacent margins are rounded and the opposite ends slightly pointed, giving the organisms a lancet shape.

Pneumococci may be divided into serotypes based on the complex polysaccharides which form their capsules. 84 serotypes have been identified by exposure to type-specific antiserum, the Neufeld quelling reaction. All are pathogenic for human beings, but types 1, 3, 4, 7, 8, and 12 are encountered most frequently in clinical practice Types 6, 14, 19, and 23 often cause pneumonia and otitis media in children but are less common in adults (Austrian, 1983, in "Harrison's Principles of Internal Medicine", Petersdorf et al., eds., 10th Edition, McGraw Hill Book Co., New York pp. 918-922). Notably, the pneumococcus is one of the three primary pathogens responsible for pneumonia, sepsis, and meningitis in children (McMillan, 1982, in "Core Textbook of Pediatrics," Kaye et al., eds., Second Edition, J. B. Lippincott Co., Philadelphia, p. 498).

2.2. Pneumococcal Vaccines

Individuals at higher than average risk of developing pneumococcal infections include patients with chronic systemic illnesses such as heart disease, chronic bronchopulmonary disease, hepatic disease, renal insufficiency, and malignancy. It is recommended that these individuals be vaccinated against pneumococcal infection. For this purpose, twenty-three vaccines comprising the capsular polysaccharides of pneumococcal types 1, 2, 3, 4, 5, 6B, 7F, 8, 9N, 9V, 10A, 11A, 12F, 14, 15B, 17F, 18C, 19A, 19F, 20, 22F, 23F, and 33F (which include serotypes or groups responsible for 90 percent of serious pneumoccal disease in the United States and the rest of the world) are available (Pneumovax®, Merck, Sharpe & Dohme, and Pnu-Immune®, Lederle Laboratories). The efficacy of this vaccine in children is questionable, as, in children younger than 6 years, immunologic responsiveness to various capsular antigens develops at different times as a result of maturational characteristics of the immune system, and protection may be of shorter duration than that observed in adults (Harrison et al., ibid). Although relatively few pneumococcus serotypes are believed to account for the majority of pediatric pneumococcal infections (Gray et al., 1979, J. Infect. Disease 140:979-983), these include types for which the maturation of the human antibody response to purified capsular polysaccharides used as vaccines is slowest (Anderson and Betts, 1989, Pediatric Infec. Dis. J. 8:S50-S53; Borgono et al., 1978, Proc. Soc. Exp. Biol. Med. 57:148-154).

2.3. Conjugate Vaccines

Immune responsiveness in human infants to *Haemophilus influenzae* b capsular polysaccharide has been achieved by coupling the capsular antigen to carrier proteins to produce a "conjugate" vaccine; it is believed that T lymphocyte helper effects are induced by the carrier protein and are responsible for the development of immunity (Robbins et al., 1984, in "Bacterial Vaccines," Germanier, ed. Academic Press, New York, pp. 289-316) See also: Cruse & Lewis, 1989 in "Conjugate Vaccines" eds. Cruse & Lewis, Karger, Basel, pp. 1-10.. A similar approach has been directed toward producing pneumococcal vaccines.

2.3.1. Intact Capsular Polymers as Antigens in Vaccines

Various investigators have isolated and purified intact capsular polymers which may be useful in or as vaccines. For example, U.S. Pat. No. 4,220,717 describes a process for the isolation and purification of immunologically active polyribosyl ribitol phosphate (PRP) from the capsular polymer of *H. influenzae* b. Additionally, U.S. Pat. No. 4,210,641 relates to polysaccharide extracts of H. influenzae having an apparent molecular weight greater than 200,000 daltons and composed principally of galactose, glucose and mannose and containing a small amount of osamines.

Several researchers have utilized these and other intact capsular polymers in formulations to achieve better immunological responses. For example, U.S. Pat. No. 4,196,192 discloses a vaccine containing purified intact PRP and a whole cell *Bordetella pertussis* vaccine formulation. This approach to increasing immunogenicity resulted in enhanced levels of anti-PRP and anti-pertussis antibodies in young mammals.

2.3.2. Use of Carrier Proteins to Make Antiserum to Haptens

Carrier proteins can do more than enhance the immunogenicity of conjugated capsular polymers; they can also render haptens immunogenic. Haptens are defined as molecules that can bind specifically to an antibody or lymphocyte receptor but may not themselves induce an immune response (i.e. they are not immunogenic). To evoke an immune response, small/low molecular weight or poorly immunogenic molecules, termed haptens, must generally first be coupled to a larger molecule, or carrier, which is usually a heterologous protein. Injection of the hapten-carrier complex into an animal will then give rise to the production by B lymphocytes of antibodies, some of which will be capable of specifically binding to the free, uncoupled hapten molecule.

Among the earliest haptens to be studied were azo dye compounds such as aniline and o-aminobenzoic acid. Landsteiner and Lampl (1918, Z. Immun. Forsch 26:293) coupled these compounds by diazotization to serum proteins. When injected with these artificially prepared azo-proteins, rabbits developed precipitating antibodies that were specific for the attached chemical moieties.

Other examples of haptenic compounds are dinitrophenol, which becomes immunogenic upon coupling as the dinitrophenyl (DNP) group to bovine serum albumin or to bovine gamma globulin (BGG), and lysergic acid diethylamide. Even formaldehyde has been shown to behave as a hapten; persons exposed to formaldehyde vapors from products or in laboratories have become "sensitized" to the compound, following the formylation of their endogenous macromolecules in vivo.

Haptenic behavior is not limited to small organic molecules, and polypeptide hormones up to the size of insulin are often poorly, if at all, immunogenic. To obtain high antibody titers to these hormones it is thus necessary to conjugate them to a carrier molecule (or to create larger molecules by crosslinking many of these polypeptides together).

The involvement of the carrier molecule is especially interesting in that the carrier plays more than a mere transport role. Ovary and Benaceraff (1963, Proc. Soc. Exp. Biol. Med. 114:723) showed this by injecting rabbits with DNP-BCG. Injection of many immunogenic materials into animals will produce an immunological "memory" of the exposure When a second injection is given later, there is thus a much more vigorous immune response. Indeed, when Ovary and Benaceraff injected DNP-BCG again, there was a strong, secondary response that led to markedly elevated levels of antibodies directed against both DNP and BCG. But when the second injection was instead made with DNP-egg albumin, a much weaker anti-DNP antibody response was noted. The difference in response was due to what has been called the carrier effect, and it appears to involve helper T lymphocytes.

Preliminary evidence indicates that all proteins may not be equally effective carrier proteins for a given hapten. Robbins, et al. (Infect. Immun. 40:245-256) have presented data on experimental protein-polysaccharide conjugate vaccines in which the same polysaccharide hapten was conjugated to different protein carriers and the antibody response to the hapten was quantified Significant differences were noted in the amount of anti-hapten antibody generated, indicating a major role for the carrier.

With respect to pneumococcal vaccines in particular, Lin and Lee (1982, Immunology 46:333) studied immune responses in adult and young mice exposed to type 6A and 19F polysaccharides as well as 19F conjugated to protein. Significantly higher IgM and IgG2 antibody titers were induced in mice receiving 19F polysaccharide-protein conjugates than in the control group receiving 19F polysaccharide alone.

2.3.3. Vaccines Containing Conjugates

Other researchers have studied conjugation of capsular polymers to carrier proteins in an effort to enhance antibody formation by the so-called "carrier effect". For example, Schneerson et al., Journal of Experimental Medicine 152:361-376 (1980) describes *H. influenzae* b polymer-protein conjugates disclosed to confer immunity to invasive diseases caused by *H. influenzae* b. The reference documents the age-related immunological behavior of capsular polymers in infants and seeks to overcome this age-dependence by conjugation of the intact capsular polymer with a variety of proteins, including serum albumins, *Limulus polyphemus hemocyanin* and diphtheria toxin. The method of conjugation involves the use of a linking agent such as adipic dihydrazide.

Geyer et al., Med. Microbiol. Immunol. 165:171-288 (1979), prepared conjugates of certain *Klebsiella pneumoniae* capsular polysaccharide fragments to a nitrophenyl-ethylamine linker by reductive amination, and the derivatized sugar was then attached to proteins using azo coupling.

U.S. Pat. No. 4,057,685 by McIntire, filed May 9, 1974 relates to an *Escherichia coli* lipopolysaccharide of reduced toxicity covalently coupled to a protein antigen by reaction with haloacyl halide.

U.S. Pat. No. 4,356,170 by Jennings et al., filed May 27, 1981, issued Oct. 26, 1982, relates to the production of polysaccharide-protein conjugates by reductive amination.

Anderson (1983, Infection and Immunity 39:233–238) relates to conjugates between oligosaccharides from *Haemophilus influenzae* type b capsular polysaccharide and $CRM_{197}$, a nontoxic but antigenically identical variant of diphtheria toxin.

Snippe et al. (1983, Infection and Immunity 42:842–844), relates to a semisynthetic vaccine to *Streptococcus pneumoniae* type 3 in which a hexasaccharide isolated from a partial acid hydrolysate of the capsular polysaccharide S3 was coupled to stearyl amine by reductive amination and then incorporated into liposomes. The resulting conjugate/liposome vaccine was observed to induce protection to *S. pneumoniae* type 3 in mice.

U.S. Pat. No. 4,663,160 by Tsay et al., filed Mar. 14, 1983, issued May 5, 1987, related to bacteria in which a detoxified polysaccharide from a gram-negative bacterium is covalently coupled to a detoxified protein from the same species of gram-negative bacterium, by means of a 4–12 carbon moiety.

U.S. Pat. No. 4,619,828 by Gordon, filed Jan. 5, 1984, issued Oct. 28, 1986, relates to conjugates between polysaccharide molecules from pathogenic bacteria such as *Haemophilus influenzae* b, *Streptococcus pneumoniae*, *Neisseria meningitidis*, and *Escherichia coli* and T cell dependent antigens such as diphtheria and tetanus toxoids.

U.S. Pat. No. 4,808,700 by Anderson and Clements, filed Aug. 10, 1984, issued Feb. 28, 1989, and U.S. Pat. No. 4,761,283 by Anderson, filed Mar. 28, 1986, issued Aug. 2, 1988, relate to the covalent attachment of capsular polymer fragments to bacterial toxins, toxoids, or binding subunits by means of reductive U.S. Pat. No. 4,711,779 by Porro et al., filed July 2, 1986, issued December 8, 1987, relates to glycoprotein conjugate vaccines having trivalent immunogenic activity and comprising antigenic determinants from the capsular polysaccharides of a gram positive bacterium and a gram negative bacterium, as well as either $CRM_{197}$, tetanus toxoid, or pertusis toxin.

2.3.4. Method for Preparing Conjugate Vaccines

The preparation of conjugate vaccines, in which capsular polysaccharide haptens are linked to carrier proteins, entails the following procedures:
(i) capsular polysaccharide must be prepared
(ii) if a fragment of the polysaccharide is to be used, it must be separated from intact polysaccharide
(iii) saccharide must be activated, or rendered amenable to conjugation, i.e. moieties capable of covalently bonding to protein must be generated
(iv) saccharide is conjugated to protein.

Various methods known in the art for accomplishing these four steps are listed in Table I.

TABLE I

| Reference | Preparation of Polysaccharide | Cleavage of Polysaccharide | Activation of Polysaccharide | Conjugation to Protein |
|---|---|---|---|---|
| U.S. Pat. No. 4,356,170 by Jennings, filed May 27, 1981 issued October 25, 1982 | | | Employed Periodic Acid to generate aldehyde groups | Reductive Amination using cyanoborohydride |
| U.S. Pat. No. 4,663,160 by Tsay et al., filed March 14, 1983, issued May 5, 1987. | | | Employed Periodic Acid to generate aldehyde groups | 1) 4–12 carbon moiety linked to protein in the presence of a condensing agent, e.g. carbodiimide ii) Polysaccharide linked to protein derivatized with 4–12 carbon moiety via a Schiff's' base reaction in the presence of a reducing agent, e.g. cyanoborohydride |
| U.S. Pat. No. 4,619,828 by Gordon, filed January 5, 1984, issued October 28, 1986 | | Polysaccharides adjusted by heat treatment to a molecular size between 200,000 and 2,000,000 daltons | *Cyanogen bromide | *Conjugated via a spacer bridge of 4–8 carbon atoms, as would exist in the adipic acid hydrazide derivative of the protein |
| U.S. Pat. No. 4,808,700 by Anderson and Clements, filed August 10, 1984, issued February 28, 1989 | | A variety of methods are used to produce antigenic fragments with at least one reducing end, e.g. limited oxidative cleavage by periodate, hydrolysis by glycosidases, or acid hydrolysis | | Conjugation via reductive amination in the presence of cyanoborohydride (approximately 2–3 weeks) |
| Section 6.5 of the above, entitled "Conjugation of Capsular Polymer Fragment of *Streptococcus Pneumoniae* to $CRM_{197}$" | Danish type 6A, Eli Lilly Co. | Acid hydrolysis in 0.1 N HCl for 10 minutes at 100° C. to generate reducing fragments | | Conjugated to $CRM_{197}$ in phosphate buffer using sodium cyanoborohydride for 18 days at 37° C. |
| U.S. Pat. No. 4,711,779 by Porro and Costantino, | | Acid hydrolysis at 100° for 6–40 hours. Haptens suitable have | Activated by introducing primary amino groups into | Conjugated to toxoid in the presence of |

TABLE I-continued

| Reference | Preparation of Polysaccharide | Cleavage of Polysaccharide | Activation of Polysaccharide | Conjugation to Protein |
|---|---|---|---|---|
| filed July 2, 1986, issued December 8, 1987. | | a molecular weight of 1000 to 2000 daltons | the terminal reducing groups (e.g. using sodium cyanoborohydride) with subsequent conversion to esters (e.g. in the presence of adipic acid derivatives) | organic solvent, e.g. dimethylsulfoxide |
| for *streptococcus pneumoniae* Type 6A | | Acid hydrolysis at 100° C. for 39 hours | Activated in ammoniacal buffer in the presence of sodium cyanoborohydride (to introduce primary amino groups) for two weeks; converted to corresponding monofunctional esters in an aqueous solution of dimethylsulfoxide containing disuccinimidyl ester of adipic acid for four hours | Conjugated to $CRM_{197}$ in the presence of dimethylsulfoxide at room temperature for 15 hours |

3. SUMMARY OF THE INVENTION

The present invention relates to the covalent attachment of oligosaccharides derived from bacterial capsular polysaccharides to carrier proteins using a novel process.

This process permits the efficient synthesis of glycoconjugates at production rates significantly faster than currently employed methods. The glycoconjugates of the invention may be used in vaccine formulations, and have been shown to be immunogenic.

In a particular embodiment, the present invention relates to production of glycoconjugates which incorporate oligosaccharides derived from *Streptococcus pneumoniae* capsular polysaccharides. The method of the invention results in the efficient production of high yields of *S. pneumoniae* glycoconjugates which may be used in vaccine formulations of particular relevance to the pediatric population, in which a large proportion of major illnesses are associated with *S. pneumoniae* infection. Immunogenic conjugates have been found to be less age dependent than capsular polymers alone, and are useful for the active immunization of very young warm-blooded mammals against systemic infections by the respective encapsulated bacteria.

In a further aspect of the invention, the glycoconjugates of the invention have, surprisingly, been found to elicit a monospecific and homogeneous immune response, which may advantageously avoid the generation of autoimmune reactions and related post-vaccination syndromes.

Importantly, the immunogenic conjugates of the invention do not contain potentially toxic linking agents, such as adipic dihydrazide or p-nitro-phenylethylamine, which have been used in conjugating carbohydrate to protein.

3.1. Abbreviations and Definitions $CRM_{197}$ a non-toxic protein antigenically cross-reactive with diphtheria toxin
DMSO dimethylsulfoxide
DP degree of polymerization
MIC minimum inhibitory concentration
SD substitution degree
SIDEA succinimidyldiester of adipic acid
SIDES succinimidyldiester of succinic acid

4. BRIEF DESCRIPTION OF THE FIGURES

FIG. 1. General strategy for synthesis of oligosaccharide-protein conjugates.
A. High molecular weight polysaccharides are acid hydrolyzed to yield oligosaccharides of an average molecular weight of $2.5 \times 10^3$.
B. Oligosaccharides are (1) activated by reaction with diaminoethane $[H_2N(CH_2)_2NH_2]$ at pH=9, reduced with pyridine borohydride ($PyBH_3$), then (2) reacted with the succinimidyl diester and adipic acid (SIDEA) in dimethylsulfoxide (DMSO).
C. Activated oligosaccharides are coupled to carrier protein via lysine residues.

Figure 2:
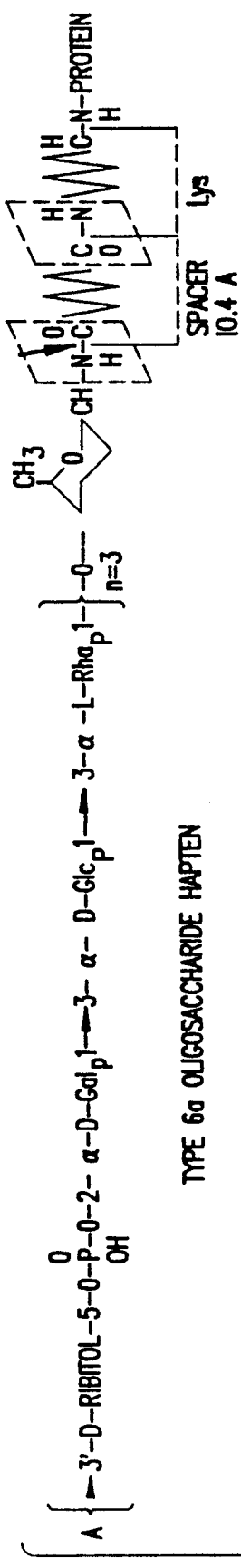
Figure 2:
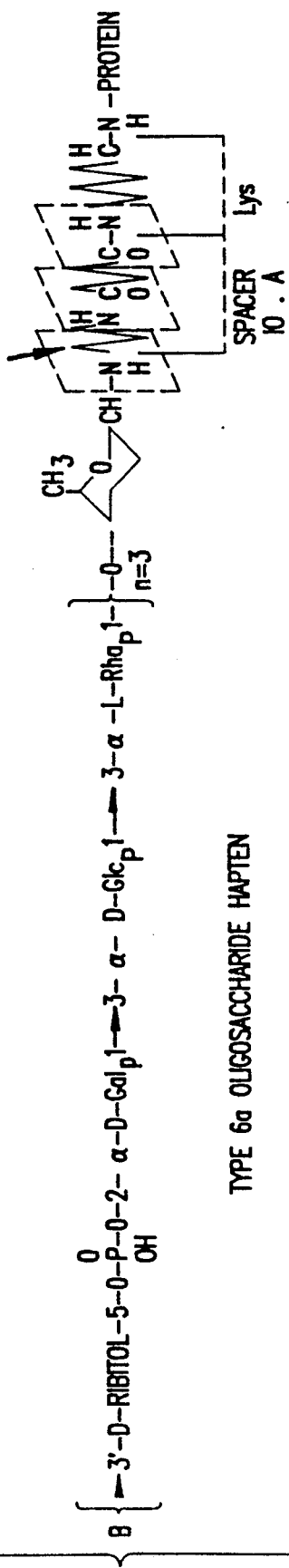
Figure 2:
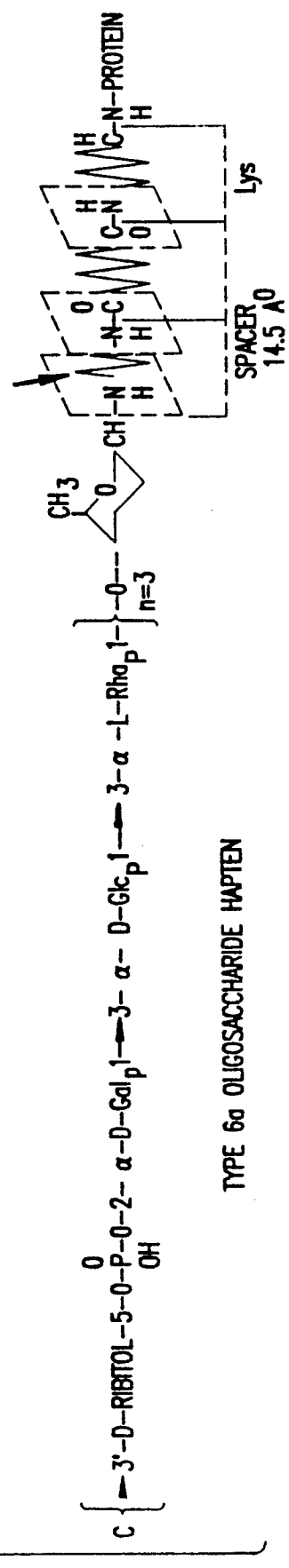

FIG. 2. Use of a "tailored" spacer in the coupling procedure.
A. Glycoconjugate formed by earlier procedure as described by Porro et al., (1985), Mol. Immunol. 22:907–919, with amide linkage (arrow) between oligosaccharide and adipic acid four carbon linker. Total length of spacer is approximately 10.4 Å.
B. Glycoconjugate formed according to the present invention in which a two carbon residue (arrow, formed by diaminoethane), and an amide linkage, exists between oligosaccharide and succinic acid two carbon linkers formed by reaction with SIDES. Total length of spacer is approximately 10 Å.
C. Glycoconjugate formed according to the present invention in which a two carbon residue (arrow, formed by diaminoethane), and an amide linkage, exists between oligosaccharide and adipic acid four carbon residue formed by reaction with SIDEA. Total length of spacer is approximately 14.5 Å.

Figure 3A:
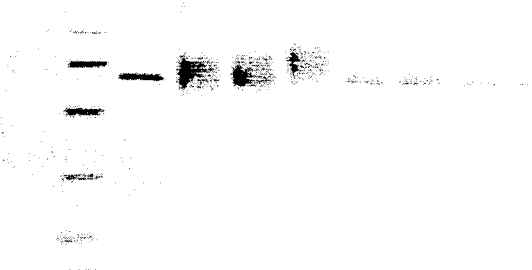
Figure 3B:
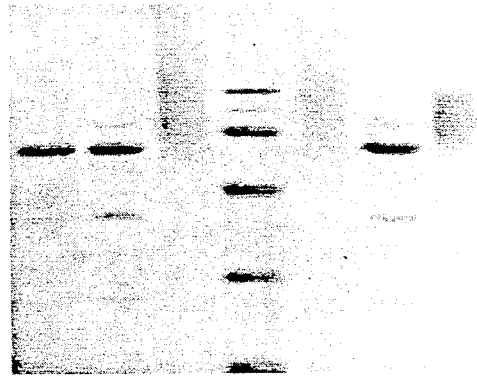
Figure 3C:

FIG. 3. Efficiency of conjugation of $CRM_{197}$ to activated oligosaccharides containing adipic acid versus succinic acid derivative spacers. SDS-polyacrylamide gel electrophoresis of products of conjugation reactions (silver stained).
A.
Lane 1: Molecular Weight Standards (92.5 K, 66.2 K, 45.0 K, 31.0 K, 21.5 K).
Lane 2: $CRM_{197}$ (1 μg) reference.

Lane 3: Conjugated oligosaccharide 6A-CRM$_{197}$ with succinic acid as spacer (2 μg) (ratio 1:1 monoester/total amino groups of CRM$_{197}$ in 50% DMSO).

Lane 4: Conjugated oligosaccharide 6A-CRM$_{197}$ with succinic acid as spacer (2 μg) (ratio: 1:2 monoester/total amino groups of CRM$_{197}$ in 50% DMSO).

Lane 5 Conjugated oligosaccharide 6A-CRM$_{197}$ with adipic acid as spacer (2 μg) (ratio: 1:2 monoester/total amino groups of C in 50% DMSO).

Lane 6: Conjugated oligosaccharide 14-CRM$_{197}$ with succinic acid as spacer (2 μg) (ratio: 1:4 monoester/total amino groups of C in 50% DMSO).

Lane 7: Conjugated oligosaccharide 19F-CRM$_{197}$ with succinic acid as spacer (2 μg) (ratio: 1:4 monoester/total amino groups of C in absence of 50% DMSO).

Lane 8: Conjugated oligosaccharide 23F-CRM$_{197}$ with succinic acid as spacer (2 μg) (ratio: 1:2 monoester/total amino groups of C in 50% DMSO).

Lane 9: CRM$_{197}$ (1 μg) reference.

B.

Lane 1: CRM$_{197}$ (1 μg) reference.

Lane 2: CRM$_{197}$ reference (1 μg, different lot compared to Lane 1)

Lane 3: Conjugated oligosaccharide 23F-CRM$_{197}$ with adipic acid as spacer (2 μg) (ratio: 1:2 monoester/total amino groups of CRM$_{197}$ in 50% DMSO).

Lane 4: Molecular Weight Standards (92.5 K, 66.2 K, 45.0 K, 31.0 K., 21.5 K).

Lane 5: Conjugated oligosaccharide 23F-CRM$_{197}$ with adipic acid as spacer (2 μg) (ratio: 1:2 monoester/total amino groups of CRM:M$_{197}$ in 50% DMSO).

Lane 6. CRM$_{197}$ (1 μg) reference CRM$_{197}$ reference (1 μg, different lot compared to Lane 1)

Lane 7: Conjugated oligosaccharide 6A-CRM$_{197}$ with adipic acid as spacer (2 μg)

C.

Lane 1: Molecular Weight Standards (92.5 K, 66.2 K, 45.0 K, 31.0 K, 21.5 K)

Lane 2: CRM$_{197}$ (1 μg) reference.

Lane 3: Conjugated oligosaccharide 6A-CRM$_{197}$ with adipic acid as spacer (2 μg)

Lane 4: Conjugated oligosaccharide 14-CRM$_{197}$ with adipic acid as spacer (2 μg)

Lane 5: Conjugated oligosaccharide 19F-CRM$_{197}$ with adipic acid as spacer (2 μg)

Lane 6: Conjugated oligosaccharide 23F-CRM$_{197}$ with adipic acid as spacer (2 μg)

Lane 7: Molecular Weight Markers (92.5 K, 66.2 K, 5.0 K, 31.0 K, 21.5 K)

Figure 4:
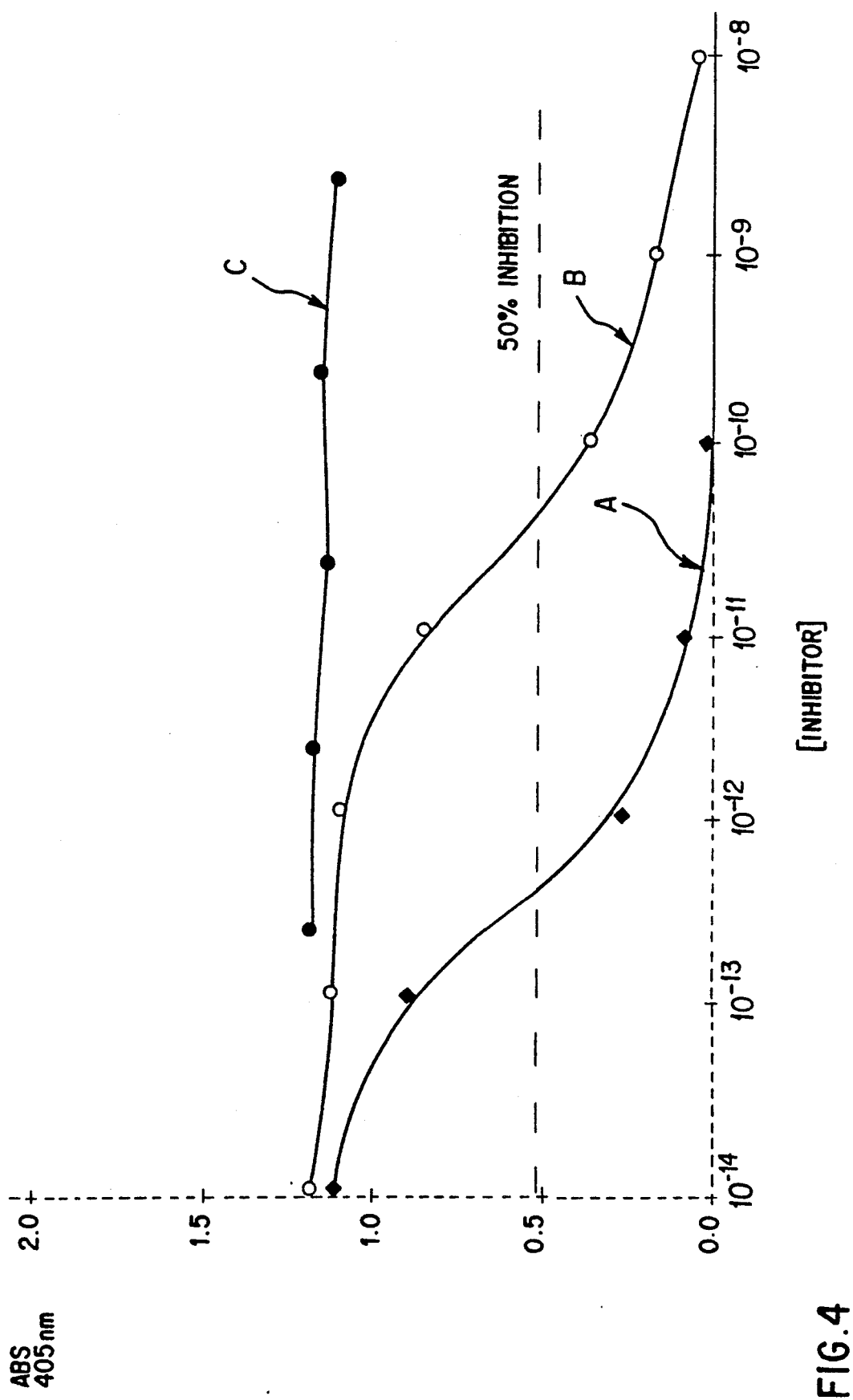

FIG. 4. Rabbit IgG response to *S. pneumoniae* oligosaccharide 6A-CRM$_{197}$ conjugates. Inhibition-ELISA analysis of affinity value of IgG isotype induced to the capsular polysaccharides.

A. Type 6A capsular polysaccharide

B. Type 6A oligosaccharide ($\overline{DP}=10$)in free form or conjugated to CRM$_{197}$ C. Type 14 oligosaccharide $\overline{DP}=12$) activated by molecular spacer or conjugated to C$_{197}$.

5. DETAILED DESCRIPTION OF THE INVENTION

The present invention relates to the covalent attachment of oligosaccharides derived from bacterial capsular polysaccharides to carrier proteins; the method of the invention generates novel glycoconjugates via a novel For clarity of disclosure, and not by way of the detailed description of the invention is divided into the following sections (i) Preparation of Oligosaccharides
(ii) Activation of Oligosaccharides
(iii) Conjugation of Oligosaccharides to Protein
(iv) Immunochemical Characterization of Glycoconjugates
(v) Vaccine Formulation and Administration
(vi) Utility of Pneumococcal Oligosaccharide Conjugate Vaccines.

5 1. Preparation of Oligosaccharides

High molecular weight capsular polysaccharide may be purchased commercially (American Type Culture Collection (Rockville, Md.)) or obtained by the methods described by Porro et al., 1983, J. Biol. Stand. 11:65-71. Any polysaccharide may be used, including, but not limited to, those found in the capsules of *Streptococcus pneumoniae, Haemophilus influenzae, Neisseria meningitidis, Escherichia coli, Salmonella typhi, Streptococcus mutans, Cryptococcus neoformans, Klebsiella pneumoniae, Staphylococcus aureus,* and *Pseudomonas aeruginosa.*

Antigenic fragments with at least one reducing end can be generated from capsular polymers by a variety of methods, depending upon the structural features of the particular capsular polymer. Limited oxidative cleavage by periodate (or related reagents) will leave aldehydic termini; such an approach will be limited to polymers having vicinal dihydroxy groups on a non-cyclic residue. Hydrolysis of a glycosidic linkage produces a reducing sugar terminus. Such hydrolysis can be most specifically accomplished enzymatically by glycosidases, but this application would be restricted to a relatively few capsular polymers, e.g. *Streptococcus pneumoniae* 8, for which glycosidases are known. Acidic hydrolysis is commonly used for hydrolysis of glycosidic linkages. The utility of this approach would be limited if the polymer contains acid-sensitive non-glycosidic linkages or if the polymer contains acid-sensitive branch linkages important to the antigenic specificity.

In specific embodiments of the invention, *S. pneumoniae* type 6A capsular polysaccharide may be hydrolyzed in approximately $10^{-2}$M acetic acid at about 100° C. for about 30 hours; *S. pneumoniae* type 14 capsular polysaccharide may be hydrolyzed in approximately 0.5M trifluoroacetic acid at about 70° C. for about 7 hours; *S. pneumoniae* type 19F polysaccharide may be hydrolyzed in approximately $10^{-2}$M acetic acid at about 50° for about 48 hours; and *S. pneumoniae* type 23F polysaccharide may be hydrolyzed in approximately 0.25M trifluoroacetic acid at about 70° C. for about 3 hours.

According to the invention, oligosaccharides to be conjugated to protein preferably consist of between three and six repeating units (or between about ten and thirty monosaccharide residues), and more preferably consist of between three and four repeating units (or about fifteen monosaccharide residues) as oligosaccharides of this length, incorporated into glycoconjugates, have been shown to be optimally immunogenic.

5.2. Activation of Oligosaccharides

Oligosaccharides may be activated by a process of reductive amination followed by reaction with a bifunctional molecule, such as, but not limited to, a diester. An outline of the method of the invention is presented in FIG. 1 and Table II, which compares the method of the present invention with the method described in Porro et al., 1985, Mol. Immunol. 22:907-919. Note that the time of activation using the former procedure was 7-14 days; this has been shortened, according to the present invention, to 15 minutes. Note also that the time of reduction using the former procedure was 7-14 days; this has been shortened, according to the present invention, to 48 hours. Accordingly, the present invention requires 12-26 fewer days to complete than the former process. This is an important advantage, as exposing carbohydrates to elevated temperatures, such as 50° C., may lead to degradation.

TABLE II

Chemical Activation of the end-reducing unit of S. pneumoniae Oligosaccharides

| Parameters | Former Procedure | Present Procedure |
|---|---|---|
| Introduced Group | $NH_2$ | $NH(CH_2)_2NH_2$ |
| Reagent (pH) | Ammoniacal buffer (9) | Diaminoethane (9) |
| Temperature of activation | 50° C. | 100° C. |
| Time of activation | 7-14 days | 15 minutes |
| Reducing agent | Na cyanoborohydride | Pyridine borane |
| Temperature of reduction | 50° C. | 50° C. |
| Time of reduction | 7-14 days | 48 hours |
| Resulting product | Oligo-$NH_2$ | Oligo-$NH(CH_2)_2NH_2$ |
| Activating Bifunctional Spacer | SIDEA (Succinimidyl diester of adipic acid | SIDES or SIDEA (succinimidyl diester of succinic or adipic acid) |
| Temperature of reaction | 25° C. | 4° C. |
| Time of reaction | 4 hours | 2 hours |
| Resulting product | Oligo-NH-Monoester | Oligo-$NH(CH_2)_2NH$-monoester |
| Efficiency of Reaction | 25-30% | 70% |

According to the method of the invention, reductive amination of the end-reducing unit of an oligosaccharide is performed using a molecule containing two amino groups. In a preferred embodiment of the invention, reductive amination is accomplished by reacting a given molar amount of oligosaccharide with a diaminoethane solution in 10X molar excess in 0.2M $KH_2PO_4$ at about pH=9 at a temperature of approximately 25°-100° C., and preferably 100° C. for between about 1-60 minutes, and preferably about 15 minutes. After that a molar amount of pyridine borane equivalent to 25 times the molar concentration of oligosaccharide in the preparation may be added and reaction is performed at between about 25°-100° C., and preferably about 50° C. for between about 1 and 72 and preferably about 48 hours.

The resulting product of the reductive amination reaction may then be reacted with a bifunctional molecule, each functional group being capable of reaction with either the terminal amino group of the activated oligosaccharide and amino groups present in the structure of the carrier protein, such that the bifunctional molecule may serve to link together the oligosaccharide and the carrier protein In a preferred embodiment of the invention, the bifunctional group is a diester, and is, more particularly, a diester of adipic acid, which has been shown to be associated with more efficient glycosylation of protein. In a preferred, specific embodiment of the invention an oligosaccharide, having been subjected to reductive amination as described supra, is reacted with a succinimidyl diester of succinic or, more preferably, adipic acid; this reaction may best be performed with the aminated oligosaccharide at a molar concentration (as amino groups) equivalent to about one-fifth of the molar concentration of SIDEA (or SIDES) in a solution of dimethylsulfoxide (DMSO) at between about 0° and 25° C., and preferably about 4° C. for between about 0.5 and 5 hours and preferably about 2 hours. The activated oligosaccharide may then be collected by precipitation using 1,4 dioxane (80% v/v), which also leaves in the supernatant the excess of SIDEA (or SIDES).

5.3. Conjugation of Oligosaccharides to Protein

Proteins which may be utilized according to the invention include any protein which is safe for administration to young mammals and which may serve as an immunologically effective carrier protein. In particular embodiments, cell surface proteins, membrane proteins, toxins and toxoids may be used. Criteria for safety would include the absence of primary toxicity and minimal risk of allergic reaction. Diphtheria and tetanus toxoids fulfill these criteria; that is, suitably prepared, they are non-toxic and the incidence of allergic reactions is acceptably low. Although the risk of allergic reaction may be significant for adults, it is minimal for infants. According to additional particular embodiments of the invention, appropriate carrier proteins include, but are not limited to, Salmonella flagellin, Hemophilus pilin, Hemophilus 15 kDa, 28-30 kDa, and 40 kDa membrane proteins, *Escherichia coli* heat labile enterotoxin LTB, cholera toxin, and viral proteins including rotavirus VP7 and respiratory syncytial virus F and G proteins.

In the "carrier effect" a weak antigen, by being attached to a stronger antigen as carrier (i.e. a heterologous protein), becomes more immunogenic than if it were presented alone. If an animal has been previously immunized with the carrier alone, the animal may be "primed" and produce an enhanced immune response not only to carrier antigen but also to attached hapten groups. Infants are routinely immunized with tetanus and diphtheria toxoids. Thus, they would be primed for subsequent presentation of a capsular polymer antigen conjugated to either of these toxoids.

In general, any heterologous protein could serve as a carrier antigen. However, certain bacterial toxins such as tetanus and diphtheria may have an additional advantage in that they are composed of two portions, one of which (the "binding" subunit) has a strong affinity for binding to mammalian cell surfaces. Conceivably, conjugation to such a "binding" protein would permit the carried antigen to more effectively initiate responses in cells of the immune system.

The carrier proteins to which the capsular polymer is conjugated may be native toxin or detoxified toxin (toxoid). Also, by relatively recent mutational techniques, one may produce genetically altered proteins which are antigenically similar to the toxin yet non-toxic. These are called "cross reacting materials", or CRMs.

$CRM_{197}$ is noteworthy since it has a single amino acid change from the native diphtheria toxin and is immunologically indistinguishable from it.

Conjugation of capsular polymer to native toxin may reduce toxicity, but significant toxicity may remain. Thus, further detoxification of protein toxins employs formalin, which reacts with free amino groups of the protein. Residual toxicity may still be a concern. Furthermore, spontaneous detoxification is possible with any particular lot of vaccine and remains an issue of concern with this approach.

Alternatively, native toxin may be detoxified with formalin to produce conventional toxoid before conjugation to capsular polymer. However, the prior formalin treatment reduces the number of free amino groups available for reaction with the reducing groups of the capsular polymer fragment. CRMs, thus, have significant advantages in that they have no inherent toxicity yet none of their amino groups are occupied by the formalin. A further advantage is that no biohazards exist in working with CRMs.

In the case of $CRM_{197}$ which is immunologically identical to native toxin, treatment with formalin (though there is no need to detoxify) greatly enhances the immunological response. It is thought that this is due to stabilization of the molecule against degradation by mechanisms of the body and/or aggregation by cross-linking (immunogenicity of particles increases with size).

For all of the above reasons, tetanus and diphtheria toxins are prime candidates for carrier proteins, yet there are others which may also be suitable. Though these others may not have the history of safety found with diphtheria and tetanus, there may be other overwhelming reasons to use them. For instance, they may be even more effective as carriers, or production economics may be significant. Other candidates for carriers include toxins of pseudomonas, staphylococcus, streptococcus, pertussis and *Escherichia coli*.

In a specific embodiment of the invention, activated oligosaccharides may be linked to $CRM_{197}$ protein which has been purified as follows:

$CRM_{197}$ produced by the strain *Corynebacterium diphtheriae*, may be separated from culture medium by passing the bacterial culture through a Millipore membrane, precipitating protein from the filtrate, and purifying $CRM_{197}$ by ion exchange chromatography, as described in section 6, infra. Alternatively, substantially pure $CRM_{197}$ may be obtained by any method known in the art.

Activated oligosaccharide may be covalently linked to carrier protein in the presence of an organic solvent and, optionally, any other agent (such as a condensing agent) in order to promote the linkage of the terminal functional group of the activated oligosaccharide to the protein. In a specific, preferred embodiment of the invention, activated oligosaccharide bearing a terminal ester group may be covalently linked to free amino groups present on carrier protein as follows:

Activated oligosaccharide may be dissolved in dimethylsulfoxide and then added to an aqueous solution of carrier protein (for example, but not limited to $CRM_{197}$ at a concentration of about 2 mg/ml) such that the molar ratio of monoester-activated oligosaccharide/total amino groups of the carrier protein is about 1:2 and the final concentration of DMSO is about 50% v/v. The conjugation reaction is performed at 4° C. and although the reaction is near to completion in about 2 hours, it is suitable to leave the reaction going overnight in order to increase the yield of reaction at the highest values for each type specific glycoconjugate. The glycoconjugates so obtained are then purified by gel chromatography.

For the synthesis of a monovalent vaccine, oligosaccharides derived from a single serotype of bacterium may be conjugated to protein. For the synthesis of a multivalent vaccine, glycoconjugates may be produced by linking a mixture of oligosaccharides derived from bacteria of different species or different serotypes to a carrier protein; alternatively, glycoconjugates produced by reacting a single type of oligosaccharide with carrier protein in separate reactions using different oligosaccharides, may be mixed. Thus, a multivalent vaccine may comprise a carrier protein bearing a homogeneous or a heterogeneous population of linked oligosaccharides.

5.4. Immunochemical Characterization of Glycoconjugates

Verification of the immunogenicity of the glycoconjugates produced by the above method may be tested in any suitable animal system prior to administration to humans, including, but not limited to rabbits, pigs, guinea pigs, mice, rats, or goats. In a specific embodiment of the invention, rabbits (approximately 2 kg in weight) may be inoculated subcutaneously with glycoproteinic conjugate in the presence or absence of aluminum phosphate or hydroxide. Approximately 2.5 $\mu$g of oligosaccharide would constitute an appropriate dose for a 2 kg rabbit. Antibody titers may then be evaluated by enzyme-linked immunosorbent assay (ELISA) or any other method known in the art. Since the antibodies generated toward the glycoconjugates of the invention may be incapable of immunoprecipitating antigen, antibody assays dependent upon immunoprecipitation are not recommended for determining titers.

5.5. Vaccine Formulation and Administration

Suitable carrier media for formulating a vaccine include sodium phosphate-buffered saline (pH 7.4) or 0.125M aluminum phosphate gel suspended in sodium phosphate-buffered saline at pH 6 and other conventional media.

Generally, vaccines containing from about 5 to about 100 $\mu$g, preferably about 10 to 50 $\mu$g of oligosaccharide, are suitable to elicit effective levels of antibody against the capsular polymer in young warm-blooded mammals. Of course, the exact dosage would be determined by routine dose/response experimentation. The concentration of the glycoproteinic conjugates for the preparation of vaccines for children is comprised within the range of about 25 to 200 $\mu$g of oligosaccharide. Greater doses may be administered on the basis of body weight. Several small doses given sequentially would be expected to be superior to the same amount of conjugate given as a single injection.

The vaccines of the invention may be administered to warm-blooded mammals of any age and are especially adapted to induce active immunization against systemic infections in young mammals caused by the pathogens *Haemophilus influenzae* type b, *Escherichia coli*, *Streptococcus pneumoniae*, *Neisseria meningitidis*, and *Pseudomonas aerugenosa*.

According to the invention, vaccine may be delivered subcutaneously, intravenously, intramuscularly, intraperitoneally, orally, or intranasally. Vaccine may comprise glycoconjugate in soluble or microparticular form, or incorporated into microspheres or microvesicles, including liposomes.

5.6. Utility of Oligosaccharide Conjugate Vaccines

In preferred embodiments of the invention, glycoconjugate vaccines directed against encapsulated pathogenic bacteria are used to protect susceptible individuals from developing infections caused by these agents. Susceptible individuals include young children with immature immune systems, asplenic individuals, as well any individual with a compromised immune system or chronic disease, particularly acquired immunodeficiency syndrome (A.I.D.S.), hematopoietic malignancy, diabetes, chronic heart disease, chronic pulmonary disease, and sickle cell anemia. The glycoconjugates of the invention, by virtue of their conjugation to a carrier protein, enhance the immunogenicity of the oligosaccharides they carry.

Thus, the glycoconjugates of the invention may be used in vaccinations to confer protection against infection with any bacteria which possesses a polysaccharide capsule, including *Streptococcus pneumoniae, Haemophilus influenzae, Escherichia coli, Neisseria meningitidis, Salmonella typhi, Streptococcus mutans, Cryptococcus neoformans, Klebsiella pneumoniae, Staphylococcus aureus,* and *Pseudomonas aerugenosa*. Strains of *S. pneumoniae* particularly virulent in children, and specifically provided for by the present invention, include types 1, 2, 3, 4, 5, 6B, 7F, 8, 9N, 9V, 10A, IIA, 12F, 14, 15B, 17F, 18C, 19A, 19F, 20, 22F, 23, and 33F.

In particular embodiments, the vaccines of the invention may be used to induce a monospecific and homogeneous immune response. A monospecific immune response is associated with a number of advantages, including providing antibodies with (i) homogeneous specificity, in which substantially all antibodies are directed against a specific epitope and are characterized by the same affinity constant value; (ii) a high affinity constant value with superior anti-bacterial activity; (iii) increased target specificity and absence of cross-reactivity with host related antigens, resulting in a safer vaccine; and (iv) decreased complement activation due to decreased precipitating activity of monospecific antibodies, also resulting in a safer vaccine.

In additional embodiments, the present invention may be used to produce vaccines which recognize peptides or lipooligosaccharide or other surface oligosaccharide haptens linked, by methods of the invention, to carrier proteins. Such vaccines may be used, for example, in the induction of immunity toward tumor cells, or in the production of anti-tumor antibodies conjugated to a chemotherapeutic or bioactive agent; such anti-tumor activity could be induced by linking a tumor-specific antigen, or epitope thereof, to a carrier protein using methods of the invention.

6. EXAMPLE: DEVELOPMENT OF A MULTIVALENT PNEUMOCOCCAL OLIGOSACCHARIDE CONJUGATE VACCINE

6.1. Preparation of Polysaccharide

*S. pneumoniae* type 6A capsular polysaccharide, *S. pneumoniae* type 14 capsular polysaccharide, *S. pneumoniae* type 19F capsular polysaccharide, and *S. pneumoniae* type 23F capsular polysaccharide were obtained from the American Type Culture Collection.

6.2. Hydrolysis of Polysaccharide

6.2.1. Hydrolysis of *S. pneumoniae* Type 6A Polysaccharide

Two milligrams of Type 6A *S. pneumoniae* capsular polysaccharide were dissolved in 1 ml. of aqueous solution containing 10 mM of acetic acid at pH=3.4, then allowed to hydrolyze in sealed ampules dipped in an oil bath at a temperature of 100° C. for thirty hours. The resulting oligosaccharides were then separated from the reaction mixture by chromatography over Sephadex G15 (Pharmacia, Uppsala) conditioned with a 15 mM solution of NaCl at ph 7.0 at 4° C.

The chromatographic effluents were then analyzed according to the procedures as reported by Kabat, (1964 in "Experimental Immunochemistry", Ed. E. A. Rabat and Mayer,pp. 538-541), Chen et al. (1956, Anal. Chem. 28:1756-1758), and Porro et a). (1981, Anal. Biochem 118:301-306) to establish the presence Of methyl-pentoses, phosphorous, and reducing groups, e.g. aldehyde groups Analysis revealed a methyl pentose/aldehyde ratio of 3.96, a methyl pentose/phosphorous ratio of 0.96, and a phosphorous/aldehyde ratio of 4.12.

Gel chromatography on Sephadex G-50 Superfine (Pharmacia ) using buffer, revealed a distribution constant (kd) of 0.538 (by hexose), corresponding to a molecular weight of approximately 2,500.

N.M.R., gas chromatography and stoichiometric analysis indicated that the oligosaccharides consisted of about 3-4 basic repeating units among which galactose, which was the immunodominant sugar, was found.

6.2.2. Hydrolysis of *S. pneumoniae* Type 14 Polysaccharide

Two milligrams of Type 14 *S. pneumoniae* capsular polysaccharide was dissolved in 1 ml. of aqueous solution containing 0.5M trifluoroacetic acid, then allowed to hydrolyze in sealed ampules dipped in an oil bath at a temperature of 70° C. for seven hours. The resulting oligosaccharides were then separated from the reaction mixture by chromatography over Sephadex G15 (Pharmacia, Uppsala) conditioned with a 15 mM solution of NaCl at pH 7.0 at 4° C.

The chromatographic effluents were then analyzed for hexosamine and aldehyde content and found to have a hexosamine to aldehyde ratio of 3.17. Gas chromatography and stoichiometric analysis indicated a molecular size corresponding to three to four basic repeating units. Debranching of galactose, as determined by gas chromatography, was within 10%. Gel chromatography on Sephadex G-50 Superfine (Pharmacia) using 15 mM NaCl at pH 7.0, revealed, for the oligosaccharide, a distribution constant (Kd) of 0.30 as determined by total hexose.

6.2.3. Hydrolysis of *S. pneumoniae* Type 19F Polysaccharide

Two milligrams of Type 19F *S. pneumoniae* capsular polysaccharide were dissolved in 1 ml. of aqueous solution containing 10 mM of acetic acid at pH=3.4, then allowed to hydrolyze in sealed ampules dipped in an oil bath at a temperature of 50° C. for forty-eight hours. The resulting oligosaccharides were then separated from the reaction mixture by chromatography over Sephadex G-15 (Pharmacia, Uppsala) conditioned with a 15 mM solution of NaCl at pH=7.0 at 4° C.

The chromatographic effluents were then analyzed according to the procedures as reported by Kabat (1964, in "Experimental Immunochemistry," Ed. E. A. Rabat and Mayer, pp. 538-541), Chen et al. (1956, Anal. Chem. 28:1756-1758), and Porro et al. (1981, Anal. Biochem. 118:301-306) to establish the presence of methyl-pentoses, phosphorous, and reducing groups, e.g. aldehyde groups. Analysis revealed a methyl pentose/reduced methyl pentose ratio of 3.5, and a methyl pentose/phosphorous ratio of 3.2.

Gel chromatography on Sephadex G-50 Superfine (Pharmacia) revealed for the oligosaccharide a $Kd=0.46$ (by total hexose) and combined analysis by gas chromatography and stoichiometry indicated a size corresponding to three to four basic repeating units.

6.2.4. Hydrolysis of S. Pneumoniae Type 23F Polysaccharide

Two milligrams of Type 23F S. pneumoniae capsular polysaccharide were dissolved in 1 ml. of aqueous solution of 0.25M trifluoroacetic acid, then allowed to hydrolyze in sealed ampules dipped in an oil bath at a temperature of 70° C. for three hours. The resulting oligosaccharides were then separated from the reaction mixture by chromatography over Sephadex G15 (Pharmacia, Uppsala) conditioned with a 15 mM solution of NaCl at pH=7.0 at 4° C.

The chromatographic effluents were then analyzed according to the procedures as reported by Kabat (1964, in "Experimental Immunochemistry," Ed. E. A. Rabat and Mayer, pp. 538-541), Chen et al. (1956, Anal. Chem. 28:1756-1758), and Porro et al. (1981, Anal. Biochem. 118:301-306) to establish the presence of methyl pentoses, phosphorous, and reducing groups, e.g. aldehyde groups. Analysis revealed a hexose/aldehyde ratio of 4.5-4.5, a hexose/methyl pentose ratio of 2.3, and a phosphorous/aldehyde ratio of 2.9.

Gas-chromatography and stoichiometric analyses indicated the presence of between 3.5 and 4.5 basic repeating units. Debranching of rhamnose, as determined by gas chromatography, was less than eight percent.

Gel chromatography on Sephadex G-50 Superfine (Pharmacia) revealed a distribution constant (Kd) of 0.38 (by hexose).

6.3. Immunochemical Characterization of S. pneumoniae Oligosaccharide Haptens The ability of S. pneumoniae type 6A, 14, 19F, and 23F oligosaccharides to interact with antibodies directed against intact capsular polysaccharides was tested as described in Porro et al. (1985, Mol. Immunol. 22:907-919), using a technique which measures the ability of a hapten (i.e. the oligosaccharide) to inhibit the homologous antigen (capsular polysaccharide) to antibody immunoprecipitation reaction (low molecular weight haptens do not give an immunoprecipitation reaction when tested toward homologous antibodies).

The method, termed "differential immunoelectrophoresis," was performed as follows: a plastic plate support for immunoelectrophoresis contained three 1% (w/v) agarose compartments (Agarose M-LKB, Bromma, Sweden). The first compartment contained 0.05% (v/v) of reference antiserum to capsular polysaccharide. The second compartment contained 0.05% (v/v) of reference antiserum to capsular polysaccharide which had previously been incubated with a known amount of reference capsular polysaccharide at 37° C. for 15 minutes. The third compartment contained 0.05% (v/v) of reference antiserum to capsular polysaccharide which had previously been incubated with a known amount of oligosaccharide hapten. An electrophoretic separation of capsular polysaccharide in four serial two-fold dilutions was then performed at 70 V/cm in 20 mM Tris-barbiturate buffer, pH=8.8, for 90 minutes. After electrophoresis, the plates were silver-stained, dried, and quantified. Inhibition by the oligosaccharide molecules was evidenced by higher "rocket" immunoprecipitates appearing in the compartment containing the reference antiserum pre-incubated with hapten. The minimal inhibitory concentration of a hapten was calculated as $$MIC_{Ha} = C_{Ha} (h_{Ag}/h_{Ha})$$

where $C_{Ha}$ = concentration of the hapten examined in the gel $h_{Ag}$ = intercept of the straight line as determined by the height of the "rocket" immunoprecipitates obtained when the reference antigen was in the gel, and $h_{Ha}$ = intercept of the straight line as determined by the height of the "rocket" immunoprecipitates obtained when the hapten examined was in the gel. Similarly, $$MIC_{Ag} = C_{Ag} \cdot h_{Ag}$$

$$\text{Specificity} = \frac{MIC_{Ag}}{MIC_{Ha}}$$

Oligosaccharide haptens of different sizes were tested.

The ability of oligosaccharides to block immunoprecipitation of capsular polysaccharides by specific antibody was also tested by the nonelectrophoretic method of radial immunodiffusion. According to this method, inhibition by oligosaccharide molecules was evidenced by a larger radius of immunoprecipitate formed by diffusion of antigen (capsular polysaccharide) through 1 percent w/v agarose containing the specific antibody previously incubated with a given amount of inhibitor (oligosaccharide). Once the Minimal Combining Concentration (MCC) for the given hapten is experimentally found, specificity is then calculated according to the previously mentioned formula:

$$\text{Specificity} = \frac{MCC_{Ag(Ps)}}{MCC_{Ha(oligo)}}$$

TABLE III

Immunochemical Characterization of S. pneumoniae Oligosaccharide Haptens

| Oligo-saccharide type | DP | MW | $(MIC_{Ps}/MIC_{Hp})$ yby DIEP | $(MCC_{Ps}/MCC_{Hp})$ by IRID |
|---|---|---|---|---|
| 6A | 2 | 1.5K | $10^{-3}$ | $10^{-3}$ |
|  | 3.5 | 2.5K | $10^{-3}$ |  |
|  | 10 | 7.0K | $10^{-1}$ |  |
| 14 | 4 | 3.5K | n.t. | $10^{-1}$ |
|  | 15 | 10.4K | n.t. | $10^{-1}$ |
| 19F | 3.5 | 2.2K | $10^{-3}$ | $10^{-4}$ |
| 23F | 3 | 2.3K | $10^{-3}$ | $10^{-2}$ |
| CH$_3$COOH (hyd) | 6 | 4.5K | $10^{-1}$ | $10^{-1}$ |

TABLE III-continued

| | Immunochemical Characterization of S. pneumoniae Oligosaccharide Haptens | | | |
|---|---|---|---|---|
| Oligo-saccharide type | DP | MW | (MIC$_P$/MIC$_{Hp}$) yby DIEP | (MCC$_P$/MCC$_{Hp}$) by IRID |
| TFA (hyd) | 4.5 | 3.4K | $10^{-4}$ | $5 \times 10^{-3}$ |
| | 9.5 | 7.2K | $10^{-1}$ | $10^{-1}$ | n.t. = not testable
DIEP = Differential Immunoelectrophoresis
IRID = Inhibition of Radial Immunodiffusion
MIC = Minimal Inhibitory Conc.
MCC = Minimal Combining Conc.

6.4. Activation of the End-reducing Unit of S. pneumoniae Oligosaccharides

Oligosaccharide haptens, obtained as described in section 6.2, supra, were dissolved in water to a final concentration of about 5 mg/ml. To each solution, 0.1 ml of 0.2M KH$_2$PO$_4$ for each milliliter of solution volume was added and the pH raised to 9.2-9.4 by the required amount of diaminomethane (generally, a volume of 2 μl diaminomethane for each milliliter of solution is required). The mixture was maintained at 100° C. for 15 minutes, upon which time an amount of about 4 μl of pyridine borane for each milliliter of solution volume was added. The pH was adjusted at 9.2 by 1N NaOH. The mixture was then transferred, in a sealed ampule, to an oil bath at 50° C. for the next 48 hours. After that, the amino-activated oligosaccharide solution was neutralized by 1N HCl and purified on Sephadex G-15 Superfine (15 mM NaCl, pH 7.01. The collected chromatographic fractions were pooled and freeze dried. Then, the freeze-dried residue was dissolved at 10 mg/ml in DMSO and added to a molar amount of SIDEA (or SIDES) corresponding to a 5:1 mol/mol ratio with respect to the amount of amino groups present in the freeze-dried compound The reaction proceeded at room temperature for 4 hours and then, was added to the solution 4 volumes of 1.4 dioxane (final conc. 80% in 1,4 dioxane) in order to precipitate the ester activated oligosaccharide. The precipitate, collected by centrifugation, was washed three times with 1,4 dioxane and kept at −20° C. or lower unless used in the conjugation process. The yield of the activation process for each of the four oligosaccharides is shown in Table IV.

TABLE IV

| | S. pneumoniae Oligosaccharide Activation: Yield of Process (% w/w) | | |
|---|---|---|---|
| Serotype | Oligo-NH(CH$_2$)$_2$NH$_2$ | Oligo-NH(CH$_2$)$_2$NH-monoester | Overall |
| 6A | 75 | 93 | 70 |
| 14 | 73 | 90 | 66 |
| 19F | 100 | 100 | 100 |
| 23F | 50 | 90 | 45 |
| Xg (±s.d.) | 74.5 (±20) | 93.3 (±4.7) | 70 (±23) |

6.5. Conjugation of Activated Oligosaccharide to CRM$_{197}$ Protein

6.5.1. Preparation of CRM$_{197}$ Protein

CRM$_{197}$, produced by Corynebacterium diphtheriae C7 (B$^{ix-197}$), was separated from culture medium by molecular filtration using a Millipore XM-50 (NMWL $5 \times 10^{-4}$) membrane. The protein was then precipitated by adding to the filtrate a saturated solution of ammonium sulfate (up to 65% w/v). Precipitated protein was collected by centrifugation, and redissolved in 0.01M phosphate buffer (pH=7.2).

Further purification of CRM$_{197}$ was achieved by ion-exchange chromatography using a 2.5×100 cm DEAE -Sepharose 6B/CL column (Pharmacia, Uppsala) conditioned in 0.01M phosphate buffer at pH 7.2, using 0.09M NaCl in 0.01M phosphate buffer as eluent.

SDS polyacrylamide gel electrophoresis under reducing conditions (Pappenheimer et al., 1972, Immunochem. 9:891-906) indicated that 80% of the CRM$_{197}$ obtained was in its native molecular form. The purity of the protein was found to be approximately 400 flocculation limit (Lf) per milligram.

6.5.2. Conjugation of Activated Oligosaccharides

The conjugation procedure consisted of couplin; the monosuccinimidyl ester-activated oligosaccharide haptens to the epsilon-amino group of the lysine residues of the carrier protein CRM$_{197}$.

Dimethyl sulfoxide containing monosuccinimidyl ester (of adipic acid) activated oligosaccharides of S. pneumoniae type 6A, 14, 19F, and 23F capsular polysaccharides was then added to a 0.1M bicarbonate solution pH=8.0 containing 2 mg/ml of CRM$_{197}$ to produce a solution which was 50% in water and in which the molar ratio of ester-activated oligosaccharide to total amino groups of the carrier protein is 1:2.

The mixture so obtained was kept, under mild stirring, at 4.C for 15 hours. Oligosaccharides from each 5of the four serotypes were conjugated to protein in separate reactions. A summary of the physiochemical characterization of the glycoconjugates obtained is presented in Table V.

TABLE V

| | Glycoconjugate Characterization | | | | |
|---|---|---|---|---|---|
| Serotype | DP oligo | MW oligo | MW conjugate (SDS-PAGE) | SD (Moles oligo/ Mole Prot. % (w/w) | Conj. Prot. |
| 6A | 3 | 2.1K | 77.6K | 7 | 100 |
| 14 | 5 | 3.5K | 85.1K | 6 | 100 |
| 19F | 3 | 1.9K | 69.2K | 4 | 100 |
| 23F | 6 | 4.5K | 85.0K | 5 | 100 |

6.5.2.1. Comparison of the Efficiency of Conjugation Using as Linker the Succinimidyl Diester of Adipic Acid Versus the Succinimidyl Diester of Succinic Acid The activated oligosaccharides formed by reaction with the succinimidyl diester of succinic acid (SIDES) were of the structure

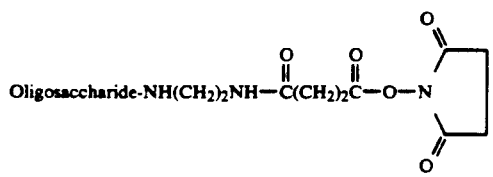

whereas those formed by reaction with the succinimidyl diester of adipic acid (SIDEA) were of the structure

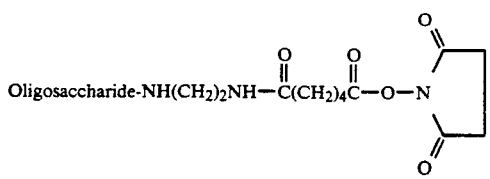

and thereby produce linkers of different sizes between oligosaccharide and conjugated protein (see FIG. 2). The efficiency of conjugation using SIDES versus SIDEA activated oligosaccharides was evaluated. As shown in FIG. 3A, B and C, only when the linker was derived from SIDEA did the protein appear to be in fully glycosylated form (where little or no free band of $CRM_{197}$ was detectable).

6.6. Immunogenicity of *S. pneumoniae* Glycoconjugates

Several formulations of the four glycoconjugate antigens were prepared and tested in rabbits (according to the schedule delineated in Table VI): type - specific glycoconjugates in monovalent formulation (2.5 or 5.0 μg oligosaccharide per dose) or multivalent formulation (2.5 μg of each oligosaccharide per dose) with and without aluminum hydroxide [Al(OH)$_3$] as mineral adjuvant (only in the multivalent formulation at 1 mg per dose were administered). Complete absorption of the four glycoconjugates to Al(OH)$_3$ occurred under the adopted conditions, since processing the supernatant of the multivalent formulation by either SDS-polyacrylamide gel electrophoresis or rocket immunoelectrophoresis did not reveal any detectable amount of free protein. An average dose of each glycoconjugate contained approximately 2.5 μg oligosaccharide and 13 μg of carrier protein $CRM_{197}$ (comparable to the average human vaccination dose of diphtheria toxoid). The immunization schedule included a priming dose and two booster doses four weeks apart. Bleedings were performed at week 0, 4, 6, and 10.

TABLE VI

Immunization Schedule For Rabbits And Mice And Doses of Vaccines

Immunization at week 0, 4, 8
Bleeding at week 0, 4, 6, 10

A. Soluble monovalent (single type) formulation
1 dose (0.5 ml): 2.5 μg oligosaccharide and
13 μg (5 Lf) $CRM_{197}$
1 dose (0.5 ml): 5.0 μg oligosaccharide and
26 μg (10 Lf) $CRM_{197}$ B. Soluble Polyvalent (mixed 4 types) formulation
1 dose (0.5 ml): 2.5 μg type-specific oligo (Tot = 10 μg oligos) and a total of 52 μg (20 Lf) $CRM_{197}$ C. Al(OH)$_3$-ads Polyvalent (mixed 4 types) formulation
1 dose (0.5 ml): 2.5 μg type-specific oligo (Tot = 10 μg oligos) and a total of 52 μg (20 Lf) $CRM_{197}$ with 1 mg of Al(OH)$_3$ Table VII shows the RIA (FARR method) estimated amount of type-specific antibodies as well as the number of responders over the number of animals immunized. The ratio (R) indicates the fold increase reached after each immunizing dose.

Table VIII shows the ELISA titers in terms of IgG isotype Ab as well as the number of responders versus the number of animals immunized. The ratios $-R_1$ $-R_2$ $-R_3$ indicate the fold increase in the titers after each immunizing dose, while the ratios $R_1$, $-R_2$, $-R_3$, indicate the fold increase in the titers for a given immunizing dose in respect to the pre-titer. Table IX reports the qualitative results in terms of functionality of the induced IgG antibodies in the recognition of the polysaccharide capsule on living streptococci (Quellung reaction or Neufeld test).

Table X shows the diphtheria toxin-neutralizing titers induced in rabbits by the carrier protein $CRM_{197}$, as estimated by Vero cells assay. Since a reference FDA antiserum was used as control, titers expressed in μ/ml have also been included.

TABLE VII

RIA-estimated titers* of rabbits immunized with oligosaccharides* of *S. Pneumoniae* type 6A, 14, 19F, 23F covalently bound to the carrier protein $CRM_{197}$****

| | Soluble Form | | | | Al(OH)$_3$-ads Form | | | |
|---|---|---|---|---|---|---|---|---|
| | week 0 | week 4 | week 6 | week 11 | week 0 | week 4 | week 6 | week 11 |
| type 6A | n.d. | n.d. | 150 (2/6) | 495 (6/6) | n.d. | 538 (5/5) | 3,190 (5/5) R = 6.0 | 4,064 (5/5) R = 1.3 |
| type 14 | n.d. | n.d. | 230 (1/6) | 195 (2/6) | n.d. | 77 (3/6) | 203 (4/5) R = 2.6 | 216 (5/5) R = 1.1 |
| type 19F | n.d. | n.d. | n.d. | 75 (6/6) | n.d. | 72 (6/6) | 108 (5/5) R = 1.5 | 188 (5/5) R = 1.7 |
| type 23F | n.d. | n.d. | 400 (1/6) | 140 (1/5) | n.d. | 283 (3/6) | n.d. | 246 (5/5) |

*Data expressed as geometric mean of titers in ngN$_{Ab}$/ml. Responders vs. total animals immunized are in parenthesis.
**Multivalent formulations of the four glycoconjugates in soluble and Al(OH)3 - adsorbed (1 mg/dose form). Each glycoconjugate contained an average of 2.5 μg of oligosaccharide and an average of 13 μg of protein $CRM_{197}$. Immunization at week 0, 4 and 9. Bleeding at week 0, 4, 6 and 11.

***type 6A and 19F oligosaccharides had an average $\overline{DP} = 3$
type 14 and 23F oligosaccharides had an average $\overline{DP} = 5$

****Glycoconjugate of type 6A had an average substitution degree $(\overline{SD})$ of oligosaccharides per unit of carrier protein (mol/mol) equal to 7.
SD for type 14 glycoconjugate was 6; for type 19F was 4 and for type 23F was 5.

TABLE VIII

ELISA Results of the IgG isotype Ab titers* induced by a multivalent vaccine including the glycoconjugates of *S. pneumoniae* $\overline{DP} = 3 + 6$ capsular oligosaccharides type 6A, 14, 19F, 23F adsorbed to the mineral adjuvant Al(OH)$_3$

| | Pre-titer (week 0) | Priming (week 4) | 1st Booster (week 6) | 2nd Booster (week 11) |
|---|---|---|---|---|
| type 6A | <50 (0/5) $R_1$ > 96.0 | 4,800 (5/5) $R_2$ = 10.7 | 51,200 (5/5) | 130,000 (5/5) $R_3$ = 2.5 (α < 0.01) |

TABLE VIII-continued

| | | ($\alpha$ < 0.01) | $R_3'$ > 2,600 | |
| --- | --- | --- | --- | --- |
| | | $R_2'$ > 1,027 | | |
| type 14 | <50 (0/5) | 360 (5/5) | 4,480 (5/5) | 19,000 (5/5) |
| | $R_1$ > 7.2 | $R_2$ = 12.4 | $R_3$ = 4.4 ($\alpha$ < 0.01) | |
| | | ($\alpha$ < 0.01) | $R_3'$ > 396.0 | |
| | | $R_2'$ > 89.3 | | |
| type 19F | <50 (0/5) | 2,080 (5/5) | 18,560 (5/5) | 35,200 (5/5) |
| | $R_1$ > 41.6 | $R_2$ = 9.0 | $R_3$ = 1.9 ($\alpha$ < 0.01) | |
| | | ($\alpha$ < 0.01) | $R_3'$ > 704.0 | |
| | | $R_2'$ > 371.2 | | |
| type 23F | <50 (0/5) | 880 (5/5) | 1,280 (5/5) | 11,880** |
| | $R_1$ > 17.6 | $R_2$ = 1.5 | $R_3$ = 9.3 ($\alpha$ < 0.01) | |
| | | ($\alpha$ < 0.01) | $R_3'$ > 237.6 | |
| | | $R_2'$ > 25.6 | | |

*Titers expressed as geometric mean of the reciprocal of the highest serum dilution showing ABS value twice of the reaction background. In parenthesis is reported the number of animals (responders over total injected).
**The value involves the titer of an unusually high responder rabbit. Discarding two out of five immunized rabbits, the best and worst responder, here are the results of the remaining 3 rabbits for the serotype 23F:

| (week 0) | (week 4) | (week 6) | (week 11) |
| --- | --- | --- | --- |
| <50 (0/5) | 667 (3/3) | 1,333 (3/3) | 2,667 (3/3) |
| $R_1$ > 13.3 | $R_2$ = 2.0 ($\alpha$ < 0.01) | $R_3$ = 2.0 ($\alpha$ < 0.01) | |
| | $R_2'$ > 26.7 | $R_3'$ > 53.3 | |

TABLE IX

Immunological Functionality of Rabbit
Serum Ab to $\overline{DP}$ = 3 − 6 Oligo-conjugated to CRM$_{197}$ Qualitative Analysis
(Quellung Reaction* for Capsular Recognition)

Type 6A *S. pneumoniae*: Positive Reaction
Type 14 *S. pneumoniae*: Positive Reaction
Type 19F *S. pneumoniae*: Positive Reaction
Type 23F *S. pneumoniae*: Positive Reaction

*Performed according to the method of Austrian (1976), Mt. Sinai J. Med. 43:699–709.

TABLE X

Antidiphtheria titers* using vero cells assay induced
in rabbits immunized by the multivalent glycoconjugates
synthesized with oligosaccharides of *S. pneumoniae*
covalently linked to the carrier protein CRM$_{197}$

| | Pre-titer (week 0) | Priming (week 4) | 1st Booster (week 6) | 2nd Booster (week 11) |
| --- | --- | --- | --- | --- |
| Soluble form | <10 | <10 | 25 (0.019 $\mu$/ml) | 1,920 (1.4 $\mu$/ml) |
| | | R = 2.5 | R = 77.0 | |
| Al(OH)$_3$-ads | <10 | 20 (0.015 $\mu$/ml) | 1,280 (0.96 $\mu$/ml) | 3,840 (2.9 $\mu$/ml) |
| | | R = 64.0 | R = 3.0 | |

FDA ref. antiserum contained 6 $\mu$/ml and gave 50% protection at dil. 1/8,000.

*Titers expressed as reciprocal of the dilution to which the pool of antisera showed 50% protection to the cells, as estimated by $^3$H-Leucine incorporation after exposure of the cells to diphtheria toxin.
Numbers in parenthesis indicate the titers in $\mu$/ml as determined using the FDA reference antiserum as control.

6.7. Oligosaccharides of Chain Length $\overline{DP}$=10–20 are Suboptimally Immunogenic Two groups of glycoconjugate vaccines were synthesized according to the scheme of synthesis described supra but using saccharides of type 6A, 14, 19F, and 23F *S. pneumoniae* with two different "range-values" of chain length, namely $\overline{DP}$=3–5 and $\overline{DP}$=10–20. The question then became whether an oligosaccharide with a chain length of $\overline{DP}$=20 or larger would also be the optimal immunogen (upon conjugation to the selected carrier protein CRM$_{197}$) in terms of priming and boosting capability as compared to a much shorter chain length, such as a $\overline{DP}$=3 oligosaccharide.

Rabbits were immunized using the protocol outlined in Table XI. As shown by comparing results presented in Tables XII and XIII, which relate to ELISA results of IgG isotype antibody titers induced by soluble *S. pneumoniae* oligosaccharides with $\overline{DP}$=10–14 and $\overline{DP}$=3–6, respectively, as well as those presented in Tables XIV and XV, which relate to ELISA results of IgG isotype antibody titers induce by *S. pneumoniae* oligosaccharides with $\overline{DP}$=10–14 and $\overline{DP}$=3–6, respectively, adsorbed to Al(OH)$_3$, a $\overline{DP}$=10–14 was not associated with enhanced immunogenicity. In fact, the IgG priming and boosting activities of $\overline{DP}$=3–5 oligosaccharide conjugates were far greater than activities observed using $\overline{DP}$=10–14 oligosaccharide conjugates. Not casually, all four carbohydrate structures investigated were associated with similar results. Further, neutralization of diphtheria toxin by glycoconjugates with $\overline{DP}$=10–14 was found to be less effective than that achieved using glycoconjugates with $\overline{DP}$=3–6 (Table XVI). Thus oligosaccharides of chain length $\overline{DP}$=10–20 are functional in conjugates of the present invention though oligosaccharides of $\overline{DP}$=3–6 elicit higher titers of antibody.

TABLE XI

Immunization Schedule for Rabbits
The models of glycoconjugates were injected at a dose of 2.5 $\mu$g carbohydrate. Since the models tested differed only in the chain length of the covalently linked oligosaccharides, the corresponding amount of carrier protein was:

| | Dose of Carbohydrate ($\mu$g) | Dose of Protein Carrier ($\mu$g) | Weigh Ratio (ww) |
| --- | --- | --- | --- |
| $\overline{DP}$ = 3 − 6 oligo-CRM$_{197}$ | 2.5 | 12.5 | 0.2 |
| $\overline{DP}$ = 10 − 14 oligo-CRM$_{197}$ | 2.5 | 2.5 | 1.0 |

Immunizational weeks 0, 4 and 8.
Bleeding at weeks 0, 4 and 10.

TABLE XII

ELISA Results of the IgG Isotype Ab Titers Induced by a
Multivalent Vaccine Including the Glycoconjugates of
*S. pneumoniae* $\overline{DP}$ = 10–14 Capsular Oligosaccharides
type 6A, 14, 19F, 23F in Soluble Form

| | Pre-titer (week 0) | Priming (week 4) | 1st Booster (week 6) | 2nd Booster (week 10) |
| --- | --- | --- | --- | --- |
| type 6A | <100 | <100 | <100 | 500 (2/5) |
| type 14 | <100 | 300 | 2,400 (3/5) | 4,600 (3/5) |
| type 19F | <100 | <100 | <100 | <100 |
| type 23F | <100 | <100 | <100 | <100 |

TABLE XIII

ELISA Results of the IgG isotype Ab titers Induced by a
Multivalent Vaccine Including the Glycoconjugates of
*S. pneumoniae* $\overline{DP}$ = 3–6 Capsular Oligosaccharides
type 6A, 14, 19F, 23F in soluble form

| | Pre-titer (week 0) | Priming (week 4) | 1st Booster (week 6) | 2nd Booster (week 11) |
| --- | --- | --- | --- | --- |
| Type 6A | <50 | <200 | 967 (6/6) $R_3$ = 8.8 ($\alpha$ <0.01) | 8,500 (6/6) |
| Type 14 | <50 | 1,800 | 3,266 (3/6) | 3,650 (4/6) |
| Type 19F | <50 | <50 | 675 (4/6) | 1,750 (6/6) |
| Type 23F | <50 | <50 | <50 | <50 |

TABLE XIV

ELISA Results of the IgG Isotype Ab Titers Induced by a Multivalent Vaccine Including the Glycoconjugates of S. pneumoniae $\overline{DP}$ = 10–14 Capsular Oligosaccharides type 6A, 14, 19F, 23F Adsorbed to the Mineral Adjuvant Al(OH)$_3$

|  | Pre-titer (week 0) | Priming (week 4) | 1st Booster (week 6) | 2nd Booster (week 10) |
|---|---|---|---|---|
| Type 6A | <100 | 240 (5/5) $R_2 = 3.8\ (\alpha < 0.01)$ $R_2' > 9.0$ | 900 (5/5) | 500 (5/5) |
| | $R_1 > 2.4$ | | | |
| Type 14 | <100 | 300 (5/5) $R_2 = 3.5\ (\alpha < 0.01)$ $R_2' > 10.4$ | 1,040 (5/5) $R_3 = 8.2\ (\alpha < 0.01)$ $R_3' > 84.9$ | 8,480 (5/5) |
| | $R_1 > 3.0$ | | | |
| Type 19F | <100 | <100 | 400 (1/5) | 800 (1/5) |
| Type 23F | <100 | <100 | <100 | 200 (1/5) |

TABLE XV

Table IV. ELISA Results of the IgG isotype AB titers* induced a multivalent vaccine including the glycoconjugates of S. pneumoniae $\overline{DP}$ = 3–6 capsular oligosaccharides type 6A, 14, 19F, 23F adsorbed to the mineral adjuvant Al(OH)$_3$

|  | Pre-titer (week 0) | Priming (week 4) | 1st Booster (week 6) | 2nd Booster (week 11) |
|---|---|---|---|---|
| Type 6A | <50 (0/5) $R_1 > 96.0$ | 4,800 (5/5) $R_2 = 10.7\ (\alpha < 0.01)$ $R_2' > 1,027$ | 51,200 (5/5) $R_3 = 2.5\ (\alpha < 0.01)$ $R_3' > 2,600$ | 130,000 (5/5) |
| Type 14 | <50 (0/5) $R_1 > 7.2$ | 360 (5/5) $R_2 = 12.4\ (\alpha < 0.01)$ $R_2' > 89.3$ | 4,480 (5/5) $R_3 = 4.4\ (\alpha < 0.01)$ $R_3' > 396.0$ | 19,800 (5/5) |
| Type 19F | <50 (0/5) $R_1 > 41.6$ | 2,080 (5/5) $R_2 = 9.0\ (\alpha < 0.01)$ $R_2' > 371.2$ | 18,560 (5/5) $R_3 = 1.9\ (\alpha < 0.01)$ $R_3' > 704.0$ | 35,200 (5/5) |
| Type 23F | <50 (0/5) $R_1 > 17.6$ | 880 (5/5) $R_2 = 1.5\ (\alpha < 0.01)$ $R_2' > 25.6$ | 1,280 (5/5) $R_3 = 9.3\ (\alpha < 0.01)$ $R_3' > 237.6$ | 11,880 (5/5) |

*Titers expressed as geometric mean of the reciprocal of the highest serum dilution showing ABS value twice of the reaction background. In parenthesis is reported the number of animals (responders over total injected).

TABLE XVI

In vitro Neutralization* of Diphtheria Toxin with Sera from Rabbits Immunized with S. pneumonia Oligosaccharide-CRM$_{197}$ Glycoconjugates

|  | Pre-titer (week 0) | Priming (week 4) | 1st Booster (week 6) | 2nd Booster (week 10) |
|---|---|---|---|---|
| $\overline{DP}$ = 3–6 oligo-CRM197: | | | | |
| Soluble | <1/10 | <1/10 | 1.20 (0.03 $\phi$/ml) | 1/1,280 (2.05 $\phi$/ml) |
| Al(OH)$_3$ads | <1/10 (0.016 $\phi$/ml) | 1/10 | 1/640 (1.02 $\phi$/ml) | 1/2,560 (4.10 $\phi$/ml) |
| $\overline{DP}$ = 10–14 oligo-CRM197: | | | | |
| Soluble | <1/10 | <1/10 | <1/10 (0.016 $\phi$/ml) | <1/10 |
| Al(OH)$_3$ads | <1/10 | <1/10 | 1/40 (0.06 $\phi$/ml) | 1/80 (0.13 $\phi$/ml) |

*Titers expressed as reciprocal of the dilution of which the pool of rabbit antisera showed 50% protection to the cells, as estimated by $^3$H-leucine incorporation after exposure of the cells to diphtheria toxin. Numbers in parenthesis indicate the titers in μg/ml as determined by the FDA reference antiserum as control.
MPL estimated in humans: 0.01 μg/ml.

6.8. The Immune Response to the Glycoconjugates is Monospecific and Homogeneous Comparison of the results depicted in Tables VII and VIII, which relate to antibody titers determined by radioimmunoassay (RIA) and enzyme linked immunosorbant assay (ELISA), reveals that the RIA estimated titers were consistently lower than ELISA-estimated titers. This observation, together with the absence of immunoprecipitates in agarose gels used for radial immunodiffusion and rocket electrophoresis analysis of anti-glycoconjugate antiserum, proves that the rabbit antisera to S. pneumoniae oligosaccharide-CRM$_{197}$ conjugates contained highly specific IgG isotype antibodies which were unable to precipitate the respective purified carbohydrate polymers used to generate the oligosaccharides.

The absence of precipitating antibodies in an antiserum is indicative of monospecificity, i.e., antibody recognition of only one epitope in the antigenic repertoire of a given molecule (Berzofsky-Schechter, 1981, Molecular Immunol. 18:751–763). Precipitation of antigen-antibody complexes requires lattice formation to generate a three-dimensional, branching network of linked antigen and antibody molecules. For this to occur, multivalency of both antigen and antibody is required, as more than one antibody must be able to bind to a single antigen molecule simultaneously. Thus, the lack of observable immunoprecipitation occurring between rabbit antiserum to S. pneumoniae oligosaccharide-CRM$_{197}$ conjugates and homologous purified high molecular weight capsular polysaccharide is strongly indicative that the antisera contained antibodies specific for the carbohydrate polymer (as shown by ELISA and inhibition-ELISA analyses) but directed toward only one determinant (epitope) of the polysaccharide.

In addition to exhibiting immunoprecipitating activity, a heterogeneous population of antibodies is also generally associated with the following property: a single epitope of the antigen used to elicit the antibody response cannot completely inhibit the binding of the entire population of antibodies to complete antigen, but will only inhibit those antibodies binding to that one epitope, leaving the other antibodies free to bind to the remaining epitopes present on complete antigen. A population of antibodies may be evaluated for heterogeneity by an ELISA-inhibition assay. In this assay, the ability of a population of antibodies to bind to complete antigen can be measured in the presence of inhibitors of antigen/antibody binding, such as isolated epitopes of the antigen. Represented graphically when the binding of antibody to labeled completed antigen is measured in the presence of increasing concentrations of unlabeled complete antigen, a sigmoidal curve is generated, which can be used as a standard curve for antibody/antigen binding. If the antibody population is heterogeneous, binding between antibody and complete antigen cannot be completely inhibited by the addition of a single antigenic epitope, and the standard curve of antibody/antigen binding is only partly displaced (partly overlapped or partly paralleled) as other antigen/antibody interactions, distinct from those associated with the epitope being tested, predominate. Conversely, binding of a homogeneous population of antibodies to antigen can be completely inhibited by the addition of an isolated epitope; the standard sigmoidal antigen/antibody binding curve for a homogeneous population of antibodies will be overlapped or paralleled by the curve generated by the addition of isolated epitope corresponding to the population's specificity.

Experimentally, by testing the *S. pneumoniae* glycoconjugate induced rabbit IgG in this manner, an affinity pattern was observed corresponding to that predicted for a homogeneous population of antibodies (FIG. 4). The *S. pneumoniae* 6A oligosaccharide, (either in non-conjugated or conjugated form), was associated with binding inhibition sigmoidal curve approximately parallel to one derived using serotype 6A high molecular weight capsular polysaccharide. As expected, a heterologous (type 14) oligosaccharide, in either free (linker-activated) or conjugated form, did not inhibit the IgG isotype population specific for the type 6A antigen.

What is claimed is:

1. A vaccine comprising a covalent conjugate of an oligosaccharide and a carrier protein for eliciting an immune response to said oligosaccharide produced by a method comprising the steps of:
   (i) reacting an oligosaccharide having a terminal reducing group with diaminomethane in the presence of pyridine borane such that reductive amination occurs; and
   (ii) reacting the aminated oligosaccharide product of (i) with a molecule comprising two functional groups, one of which is capable of reacting with the terminal group of the activated oligosaccharide and the other which is capable of reacting with said carrier protein; and
   (iii) reacting the activated oligosaccharide product of (ii) with said carrier protein such that conjugation occurs.

2. A method of inducing immunity to an oligosaccharide in a mammal comprising administering an effective amount of a vaccine according to claim 1 to said mammal.

* * * * *